(12) United States Patent
Kim et al.

(10) Patent No.: US 8,944,246 B2
(45) Date of Patent: Feb. 3, 2015

(54) DETECTING DEVICE PACKING TRAY

(75) Inventors: Do Gyoon Kim, Seongnam-si (KR); Jin Tae Kim, Hwaseong-si (KR); Jong Gun Lee, Suwon-si (KR); Hyun Min Kim, Gwangju-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 407 days.

(21) Appl. No.: 13/168,368

(22) Filed: Jun. 24, 2011

(65) Prior Publication Data

US 2012/0160792 A1 Jun. 28, 2012

(30) Foreign Application Priority Data

Dec. 28, 2010 (KR) .................. 10-2010-0136432

(51) Int. Cl.
| | | |
|---|---|---|
| *A61B 17/06* | (2006.01) | |
| *A61B 19/02* | (2006.01) | |
| *A61L 15/00* | (2006.01) | |
| *G01N 33/53* | (2006.01) | |
| *G01N 33/543* | (2006.01) | |

(52) U.S. Cl.
CPC ...... *G01N 33/5302* (2013.01); *G01N 33/54366* (2013.01)
USPC ......................................... 206/438; 206/564

(58) Field of Classification Search
USPC ............. 206/438, 528, 459.1, 472, 204, 303, 206/310, 308.1, 5.1; 211/71.01, 133.6, 13.1
See application file for complete search history.

(56) References Cited

U.S. PATENT DOCUMENTS

| | | | | |
|---|---|---|---|---|
| 3,949,872 | A * | 4/1976 | Paudras | 206/310 |
| 5,299,186 | A * | 3/1994 | Tsurushima | 206/308.1 |
| 5,320,219 | A * | 6/1994 | Ward | 206/224 |
| 5,894,924 | A * | 4/1999 | Koch | 206/310 |
| 6,227,363 | B1 * | 5/2001 | Lu | 206/308.1 |
| 6,283,283 | B1 * | 9/2001 | Rufo et al. | 206/308.1 |
| 6,446,797 | B1 * | 9/2002 | Shiga | 206/303 |
| 6,626,289 | B2 * | 9/2003 | Nagata et al. | 206/307.1 |
| 2001/0000599 | A1 * | 5/2001 | Belden, Jr. | 206/310 |
| 2001/0052474 | A1 * | 12/2001 | Kuremoto et al. | 206/308.1 |
| 2002/0056654 | A1 * | 5/2002 | Carman et al. | 206/308.1 |
| 2002/0112974 | A1 * | 8/2002 | Lau | 206/308.1 |
| 2004/0074790 | A1 * | 4/2004 | Kuremoto et al. | 206/308.1 |
| 2004/0079657 | A1 * | 4/2004 | Yau et al. | 206/308.1 |
| 2004/0118740 | A1 * | 6/2004 | Donegan | 206/528 |
| 2007/0062828 | A1 * | 3/2007 | Edwards et al. | 206/308.1 |

* cited by examiner

*Primary Examiner* — Luan K Bui
*Assistant Examiner* — Rafael Ortiz
(74) *Attorney, Agent, or Firm* — Sughrue Mion, PLLC

(57) ABSTRACT

A detecting device packing tray is provided which prevents a detecting device from being contaminated and damaged. The detecting device packing tray includes a tray main body configured to support a detecting device including a detection region to detect a reaction result. The tray main body includes a non-contact groove provided at a position corresponding to the detection region of the detecting device when the detecting device is supported by the tray main body so that the detection region does not contact the tray main body.

16 Claims, 4 Drawing Sheets

DETECTING DEVICE PACKING TRAY

CROSS-REFERENCE TO RELATED APPLICATION

This application claims the benefit of Korean Patent Application No. 2010-0136432, filed Dec. 28, 2010 in the Korean Intellectual Property Office, the disclosure of which is incorporated herein by reference.

BACKGROUND

1. Field

Exemplary embodiments relate to a detecting device packing tray used in biochemical inspection, which prevents a detecting device from being contaminated and damaged during distribution and use of the detecting device.

2. Description of the Related Art

In general, detecting devices are used to perform various inspections including biochemical reaction and to detect results of these inspections. A bio disc is detecting device and has a disc shape. Within the bio disc, chambers to accommodate a fluid, channels along which the fluid moves, and microfluidic structures, such as valves to control movement of the fluid, are provided.

A sample injected into the bio disc biochemically reacts with a reagent within the bio disc. Further, a detection region is provided on the bio disc to detect a result of such biochemical reaction. The detection region includes a plurality of chambers to accommodate reaction result substances.

The bio disc is packaged in a pouch for distribution. When the bio disc randomly moves within the pouch during distribution, the surface of the bio disc may be scratched due to friction with an inner surface of the pouch. If the outer surface of the detection region becomes scratched, this may influence a detection result during use of the bio disc.

Further, in order to adjust humidity within the pouch, a dehumidifying agent, such as silica gel, may be packed along with the bio disc in the pouch. When the dehumidifying agent moves within the pouch during distribution, the bio disc may be damaged.

SUMMARY

One or more exemplary embodiments provide a detecting device packing tray, which prevents a detection region of a detecting device from being contaminated and damaged.

In accordance with an aspect of an exemplary embodiment, there is provided a detecting device packing tray including a tray main body configured to support a detecting device including a detection region to detect a reaction result, and a non-contact groove provided on the tray main body so that the detection region does not contact the tray main body.

A central hole having a designated diameter may be provided at the center of the detecting device, and the tray main body may include fixing protrusions connected to the central hole so as to fix the detecting device.

The detection region may include a plurality of chambers disposed in the radial direction from the center of the detection device, and the non-contact groove may have a ring shape corresponding to the detection region.

The detecting device packing tray may further include a dehumidifying agent case on which a dehumidifying agent to protect the detecting device from moisture is mounted.

The dehumidifying agent case may include a dehumidifying agent accommodation recess to accommodate the dehumidifying agent, and a dehumidifying agent cover to open and close an inlet of the dehumidifying agent accommodation recess.

The dehumidifying agent cover may be rotatably connected to the tray main body.

The dehumidifying agent case may further include a dehumidification hole communicating the inner space of the dehumidifying agent accommodation recess with the outside of the dehumidifying agent accommodation recess.

The detecting device packing tray may further include a tray cover provided to cover at least a part of the detecting device placed on the tray main body.

The tray cover may be rotatably connected to the tray main body, and be connectable to the tray main body so as to prevent separation of the detecting device from the tray main body.

The tray cover may include a connection protrusion provided so as to be connected to the fixing protrusions.

The tray main body may include an inner support plane to support the central portion of the detecting device and an outer support plane to support the edge portion of the detecting device, and the non-contact groove may be located between the inner support plane and the outer support plane in the radial direction of the detecting device.

The tray main body may further include a separation protrusion disposed at the outside of the outer support plane in the radial direction of the detecting device, and a height of the separation protrusion may be greater than a height of the detecting device.

In accordance with an aspect of another exemplary embodiment, there is provided a detecting device packing tray including a tray main body configured to support a lower surface of a detecting device so that the detecting device is placed on the tray main body, an inner support plane disposed close to the center of the detecting device to support the detecting device, an outer support plane disposed more distant from the center of the detecting device than the inner support plane in a radial direction to support the detecting device, and a non-contact groove provided on the tray main body so that at least a part of the lower surface of the detecting device does not contact the tray main body, wherein the non-contact groove is located between the inner support plane and the outer support plane in the radial direction of the detecting device.

The non-contact groove may have a ring shape.

The detecting device packing tray may further include a tray cover rotatably connected to the tray main body so as to cover at least a part of the upper surface of the detecting device, and provided so as to be connectable to the tray main body.

In accordance with an aspect of another exemplary embodiment, there is provided a detecting device packing tray to pack a detecting device provided with a central hole includes a tray main body configured to support a lower surface of the detecting device so that the detecting device is placed on the tray main body, fixing protrusions provided on the tray main body so as to fix the detecting device to the tray main body and connected to the central hole, a non-contact groove provided on the tray main body so that at least a part of the lower surface of the detecting device does not contact the tray main body, and a tray cover rotatably connected to the tray main body so as to cover at least a part of an upper surface of the detecting device.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
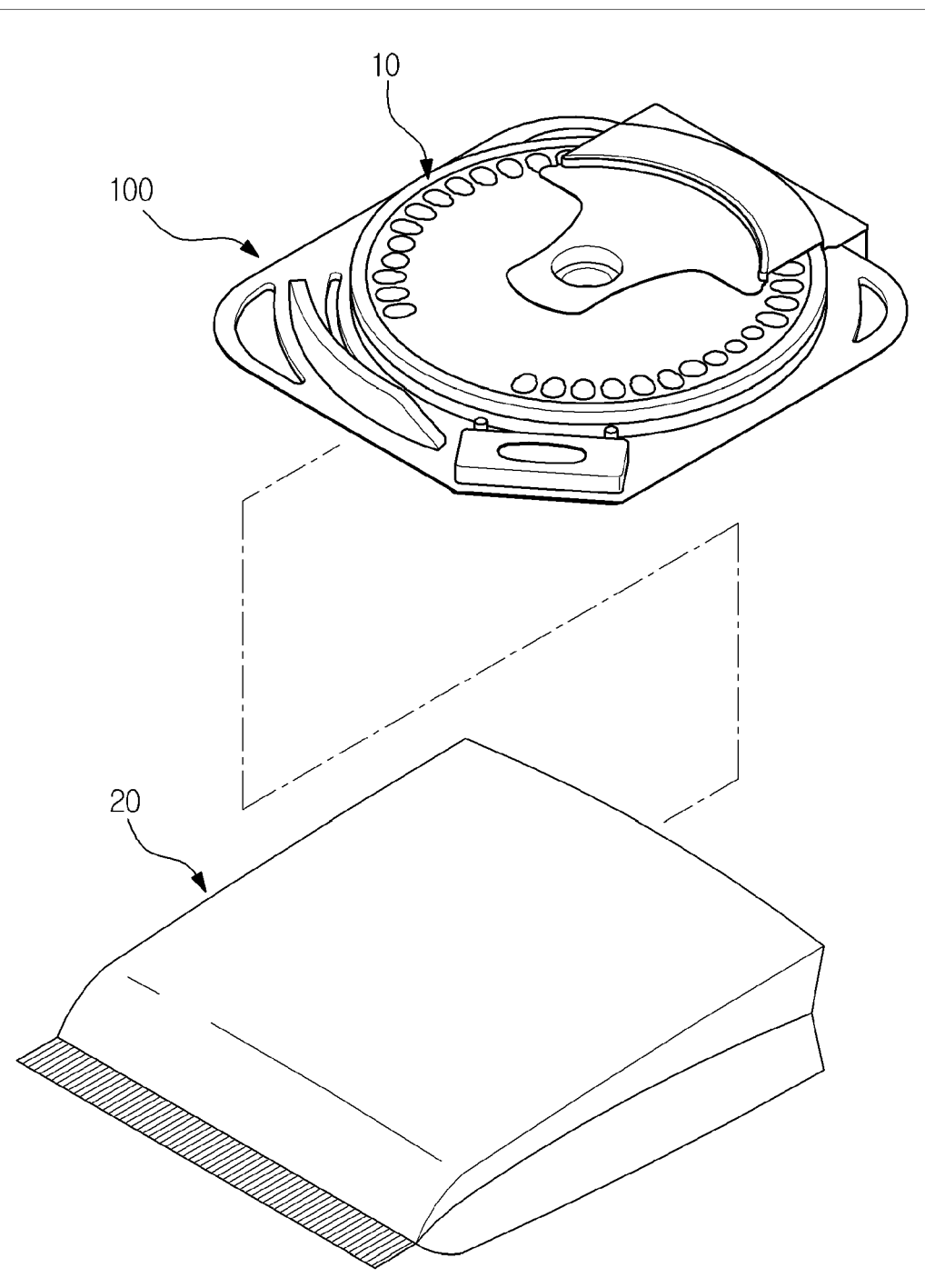
FIG. 1 is a view illustrating a main configuration of a tray on which a bio disc is placed in accordance with an exemplary embodiment.

Exemplary embodiments will be described in detail to with reference to the accompanying drawings, wherein like reference numerals refer to like elements throughout. Although the exemplary embodiments may be applied to detecting devices having various shapes, a bio disc having a disc shape will be exemplarily described below.

Figure 2:
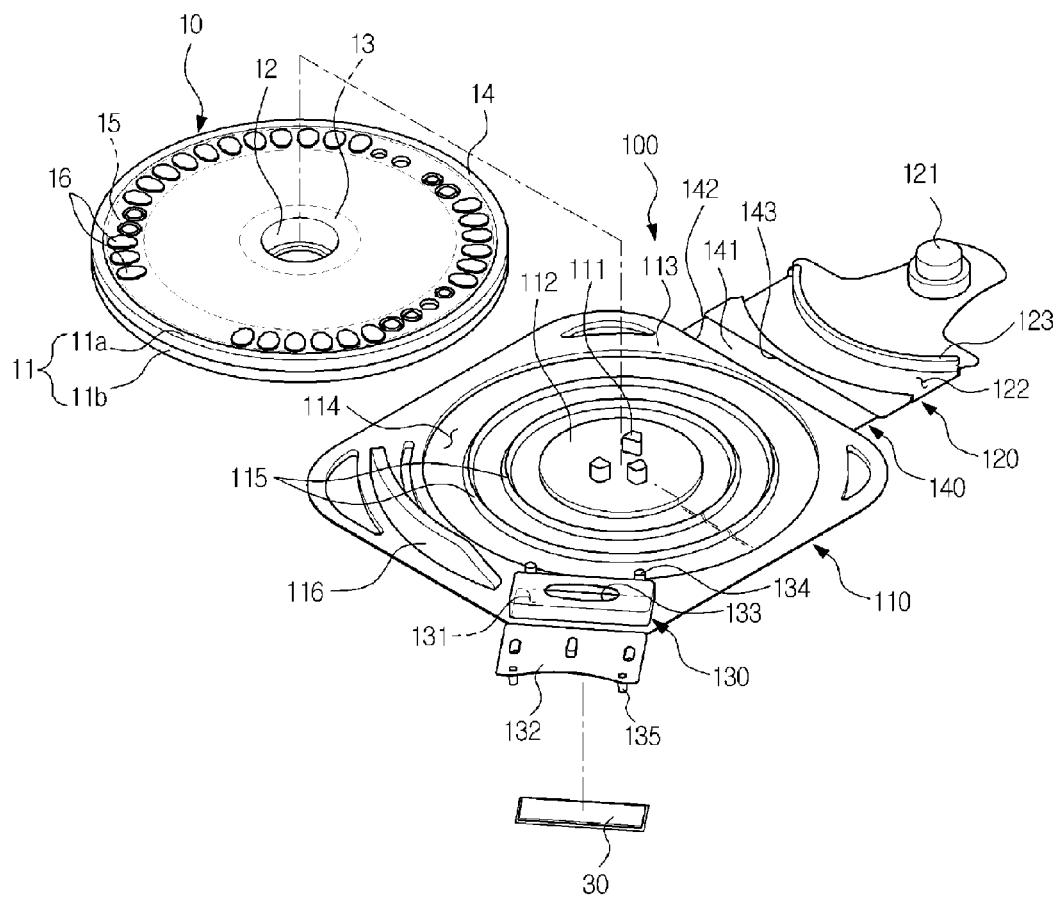
FIG. 2 is a view illustrating the main configuration of the tray from which the bio disc is separated in accordance with an exemplary embodiment.
Figure 3:
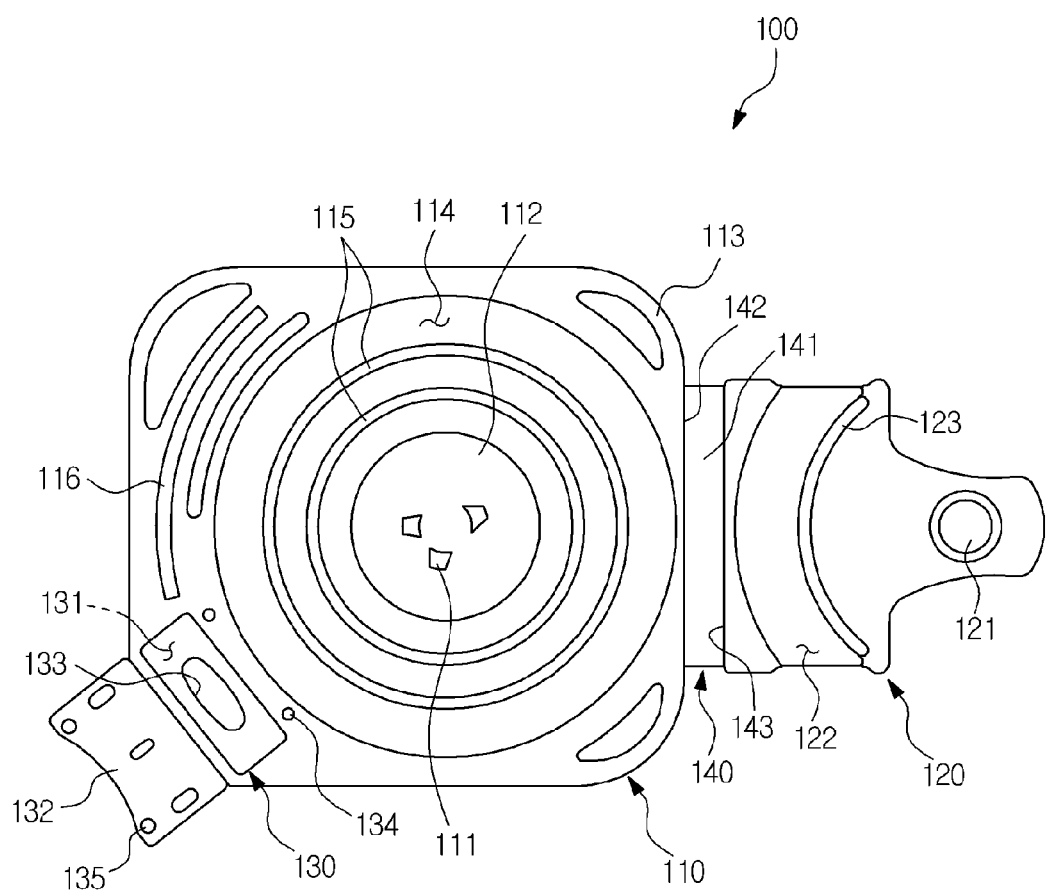
FIG. 3 is a plan view illustrating the main configuration of the tray in accordance with an exemplary embodiment.

FIG. 1 is a view illustrating a main configuration of a tray on which a bio disc is placed in accordance with an exemplary embodiment, FIG. 2 is a view illustrating the main configuration of the tray from which the bio disc is separated in accordance with an exemplary embodiment, and FIG. 3 is a plan view illustrating the main configuration of the tray in accordance with an exemplary embodiment.

As shown in FIGS. 1 to 3, a bio disc 10 is packed in a pouch 20 under the condition that the bio disc 10 is fixed to a tray 100. Further, the pouch 20 is maintained in a sealed state so that the bio disc 10 is not exposed to external environments during distribution.

The bio disc 10 includes a platform 11 having a disc shape, a plurality of chambers separated from each other within the platform 11 so as to accommodate a fluid, and a plurality of channels through which the fluid flows. Further, a central hole 12 having a designated diameter is provided in the bio disc 10 so as to mount the bio disc 10 on a rotating device (not shown) configured to rotate the bio disc 10.

The platform 11 may be formed of a plastic material, such as acryl or PDMS, which is easily molded, and has surface which is biologically inactive. However, material forming the platform 11 is not limited thereto and the platform may be formed of any suitable material having chemical and biological stability, optical transparency and mechanical processability.

The platform 11 includes a plurality of stacked plate layers. Intaglio structures corresponding to the chambers or the channels are formed at an interface between the plates, and the plates are bonded, thereby forming spaces and paths within the platform 11. For example, the platform 11 may be include an upper plate 11a and a lower plate 11b attached to the upper plate 11a. The platform 11 may further include a divisional plate (not shown) disposed between the upper plate 11a and the lower plate 11b to define the chambers to accommodate the fluid and the channels along which the fluid flows. In addition, the platform 11 may have various shapes.

The upper plate 11a and the lower plate 11b may be bonded together by various methods including adhesion using an adhesive agent or a double-sided adhesive tape, ultrasonic fusion and laser fusion.

Further, the bio disc 10 includes a plurality of detection chambers 16 to accommodate reaction result substances so that a result of reaction generated within the bio disc 10 may be detected from the outside. The result of the reaction may be detected by irradiating light of a specific wavelength onto the detection chambers 16, receiving light having passed through the detection chambers 16 and then observing variation of the wavelength of the light.

The plurality of detection chambers 16 are arranged in the radial direction of the bio disc 10 and is thus located at a ring-shaped region which is defined as a detection region 15. That is, the detection region 15 includes the plurality of detection chambers 16.

When damage to the detection region 15, such as scratches, or contamination of the detection region 15, occurs due to foreign substances during distribution of the bio disc 10, reliability of the result of the reaction detected from the detection region 15 may be lowered. Therefore, the bio disc 10 is distributed under the condition that it is placed on the tray 100, and the detection region 15 of the bio disc 10 is protected by the tray 100 during distribution.

The tray 100 includes a tray main body 110 on which the bio disc 10 is placed, a tray cover 120 connected to the tray main body 110, and a dehumidifying agent case 130 in which a dehumidifying agent 30 is fixedly held.

The tray 100 is formed of a material, the surface of which is smooth, so as to prevent damage to the bio disc 10. For example, the tray 100 may be formed of synthetic resin, such as plastic. Further, the tray 100 may be formed of a transparent or semi-transparent material so that a user can visually confirm the state of the bio disc 10 under the condition that the bio disc 10 is placed on the tray 100.

The tray main body 110 includes fixing protrusions 111 to fix the bio disc 10, support planes 112 and 113 on which the bio disc 10 is placed, and a non-contact groove 114 located under the detection region 15.

The fixing protrusions 111 are located so as to correspond to the central hole 12 of the bio disc 10. The bio disc 10 is fixed to the tray main body 110 by connecting the plural fixing protrusions 111 to the central hole 12. The bio disc 10 and the fixing protrusions 111 may be connected through various connection methods, such as insertion connection and hook connection. Although a plurality of fixing protrusion are shown in FIGS. 2 and 3, the number of the fixing protrusions 111 is not limited and, only one fixing protrusion may be provided.

The support planes 112 and 113 contact the lower surface of the bio disc 10, thus supporting the bio disc 10. The support planes 112 and 113 include an inner support plane 112 located around the fixing protrusions 111 and an outer support plane 113 located at the outside of the inner support plane 112 based on the fixing protrusions 111. That is, the support planes 112 and 113 support the bio disc 10 at at least two points separated from each other by a designated distance so as to stably support the bio disc 10 on the tray main body 110.

The inner support plane 112 has a circular shape and the fixing protrusions 111 are located on the inner support plane 112. A central portion 13 of the bio disc 10 located around the central hole 12 of the bio disc 10 is supported by the inner support plane 112. Further, an edge portion 14 of the bio disc 10 distant from the central hole 12 of the bio disc 10 in the radial direction is supported by the outer support plane 113.

The non-contact groove 114 of the tray main body 110 is provided between the inner support plane 112 and the outer support plane 113. That is, the inner support plane 112 and the outer support plane 113 are separated from each other such that the non-contact groove 114 is located between the inner support plane 112 and the outer support plane 113. The non-contact groove 114 is provided at a position corresponding to the detection region 15 so that the detection region 15 of the bio disc 10 does not contact the tray main body 110 under the condition that the fixing protrusions 111 of the tray main body 110 are connected to the central hole 12 of the bio disc 10.

The detection region 15 of the bio disc 10 has a ring shape extended from the central hole 12, and thus the non-contact groove 114 of the tray main body 110 has a ring shape corresponding to the shape of the detection region 15. The tray main body 110 is disposed between the inner surface of the pouch 20 and the detection region 15 of the bio disc 10 to prevent the detection region 15 of the bio disc 10 from being damaged by friction with the pouch 20, and includes the non-contact groove 114 to prevent the detection region 15 of the bio disc 10 from being damaged due to contact with the tray main body 110.

A plurality of support protrusions 115 having a ring shape are provided on the non-contact groove 114. A height of the support protrusions 115 of the tray main body 110 corresponds to a depth of the non-contact groove 114. Therefore, the support protrusions 115 of the main body 110 support the lower surface of the bio disc 10 at the same height as the support planes 112 and 113. The plurality of support protrusions 115 are disposed concentrically based on the fixing protrusions 111. Further, the support protrusions 115 serve to increase torsional rigidity of the tray main body 110 as well as to support the bio disc 10.

Further, the tray main body 110 includes a separation protrusion 116. The separation protrusion 116 will be described later.

The tray cover 120 includes a connection protrusion 121 provided so as to be connected to the tray main body 110, a non-contact groove 122 provided so as to be located above the detection region 15 of the bio disc 10, and a support protrusion 123 to support the bio disc 10 from the top.

The tray cover 120 covers at least a part of the upper surface of the bio disc 10. When the bio disc 10 is placed on the tray main body 110 and then the upper surface of the bio disc 10 is covered with the tray cover 120, a person may handle the bio disc 10 together with the tray 100 simply by grasping the tray main body 110 and the tray cover 120 without directly grasping of the bio disc 10. Therefore, contamination of the detection region 15 of the bio disc 10 due to worker's grasping during a process of packing the bio disc 10 and a process of using the bio disc 10 may be prevented.

The tray cover 120 may cover the entirety of the upper surface of the bio disc 10 in the same manner as the tray main body 110. However, the tray cover 120 in accordance with the exemplary embodiment covers only a part of the upper surface of the bio disc 10. Instead, the tray main body 110 includes the separation protrusion 116 provided at the opposite side of the tray cover 120 with respect to the fixing protrusions 111. A height of the separation protrusion 116 extending from the support planes 112 and 113 is greater than at least a thickness of the bio disc 10, i.e., a height of the bio disc 10. Therefore, when the bio disc 10 is packed in the pouch 20 under the condition that the bio disc 10 is fixed to the tray 100, the separation protrusion 116 of the tray main body 110 supports the inner surface of the pouch 20, thereby preventing the inner surface of the pouch 20 from contacting the detection region 15 of the bio disc 10, which is not covered with the tray cover 120. Therefore, although the tray cover 120 does not cover the entirety of the upper surface of the bio disc 10, the upper surface of the detection region 15 of the bio disc 10 does not contact the inner surface of the pouch 20, and thus materials necessary to manufacture the tray 100 may be reduced.

The connection protrusion 121 fixes the tray cover 120 to the tray main body 110. The connection protrusion 121 is connected to the fixing protrusions 111 of the tray main body 110, thereby fixing the tray cover 120 to the tray main body 110. The outer surfaces of the plural fixing protrusions 111 of the tray main body 110 are connected to the central hole 12 of the bio disc 10, and the inner surfaces of the plural fixing protrusions 111 are connected to the connection protrusion 121. However, connection between the connection protrusion 121 and the fixing protrusions 111 is not limited thereto and various other connection methods may be employed. Connection between the tray cover 120 and the tray main body 110 may be also carried out through various connection methods.

The non-contact groove 122 provided on the tray cover 120 is provided at a position corresponding to the detection region 15 of the bio disc 10 under the condition that the tray cover 120 is connected to the tray main body 110. Therefore, the detection region 15 of the bio disc 10 does not contact the tray cover 120 by the non-contact groove 122. Since the detection region 15 of the bio disc 10 has a ring shape, the non-contact groove 122 has an arc shape centering around the connection protrusion 121.

Further, the tray cover 120 includes the support protrusion 123 to support the upper surface of the bio disc 10 under the condition that the tray cover 120 is connected to the tray main body 110. The support protrusion 123 has an arc shape centering around the connection protrusion 121, and is located to be closer to the connection protrusion 121 than the non-connection groove 122 of the tray cover 120 so that the support protrusion 123 does not contact the upper surface of the detection region 15 of the bio disc 10.

A connection unit 140 is rotatably connected to the tray main body 110 and the tray cover 120. The tray cover 120 is rotatably connected to the tray main body 110 by the connection unit 140. A thickness of a connection region 142 between a body 141 of the connection unit 140 and the tray main body 110 and a thickness of a connection region 143 between the body 141 of the connection unit 140 and the tray body 120 may be smaller than a thickness of the body 141 of the connection unit 140 so that the tray main body 110 and the tray cover 120 are easily rotated with respect to each other. Further, a groove may be formed on each of the connection regions 142 and 143 so that the connection regions 142 and 143 may be easily bent.

The dehumidifying agent case 130 includes a dehumidifying agent accommodation recess 131 to accommodate the dehumidifying agent 30, and a dehumidifying agent cover 132 to open and close an inlet of the dehumidifying agent accommodation recess 131. The dehumidifying agent 30 provided as a pack type may be accommodated in the dehumidifying agent case 130.

The dehumidifying agent case 130 is formed integrally with the tray 100. Although FIGS. 1 to 3 illustrate the dehumidifying agent case 130 as being provided on the tray main body 110, the dehumidifying agent case 130 may be provided on the tray cover 120. Alternatively, the dehumidifying agent case 130 may be provided separately from the tray 100 and then be connected to the tray main body 110 or the tray cover 120.

The dehumidifying agent accommodation recess 131 is provided on the tray main body 110. The dehumidifying agent accommodation recess 131 is disposed at the outside of the outer support plane 113 of the try main body 110 based on the fixing protrusions 111 of the tray main body 110. The dehumidifying agent cover 132 is rotatably or foldably connected to the tray main body 110. A connection region between the dehumidifying agent cover 132 and the tray main body 110 is formed so as to be easily bent in the same manner as the connection regions 142 and 143 of the connection unit 140. The dehumidifying agent 30 is fixedly mounted on the tray 100 by rotating or folding the dehumidifying agent cover 132 to close the dehumidifying agent accommodation recess 131 under the condition that the dehumidifying agent 30 is accommodated in the dehumidifying agent accommodation recess 131.

Closing protrusions 135 are provided on the dehumidifying agent cover 132 and closing holes 134 to which the closing protrusions 135 are connected are provided around the dehumidifying agent accommodation recess 131 of the tray main body 110 so that the closed state of the inlet of the dehumidifying agent accommodation recess 131 by the dehumidifying agent cover 132 is maintained.

A dehumidification hole 133 communicating the inner space of the dehumidifying agent accommodation recess 131 with the outside of the dehumidifying agent accommodation recess 131 is provided on the dehumidifying agent case 130. The dehumidification hole 133 is formed in the dehumidifying agent accommodation recess 131. The dehumidification hole 133 may be formed on the dehumidifying agent cover 132.

Figure 4:
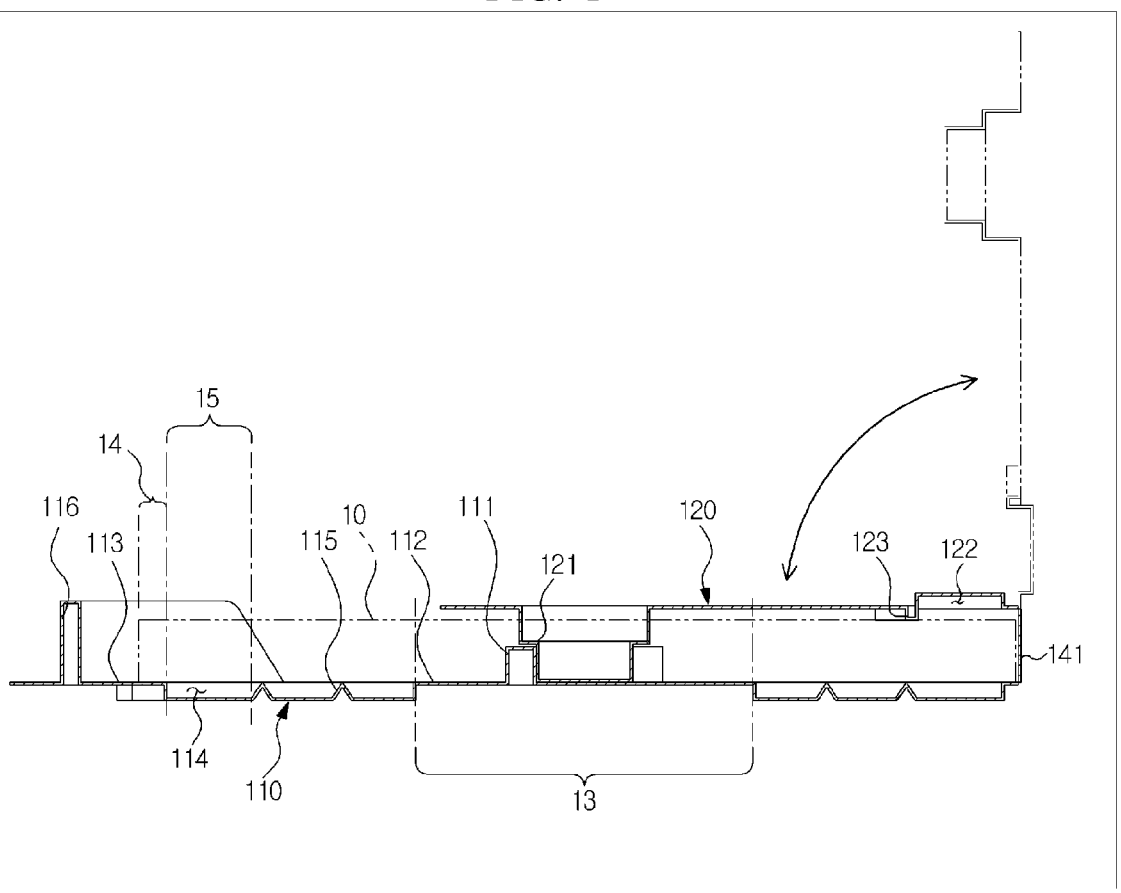
FIG. 4 is a cross-sectional view of the tray on which the bio disc is placed in accordance with an exemplary embodiment.

FIG. 4 is a cross-sectional view of the tray in accordance with the embodiment of the present invention on which the bio disc is placed.

As shown in FIG. 4, the tray cover 120 is rotated under the condition that the bio disc 10 is placed on and fixed to the tray main body 110, thus being connected to the tray main body 110.

The central portion 13 of the bio disc 10 is supported by the inner support plane 112 of the tray main body 110, and the edge portion 14 of the bio disc 10 is supported by the outer support plane 113 of the try main body 110. Further, the detection region 15 of the bio disc 10 does not contact the tray main body 110 by the non-contact groove 114 of the tray main body 110 located under the detection region 15.

Under the condition that the connection protrusion 121 of the tray cover 120 is connected to the fixing protrusions 111 of the tray main body 110, the separation protrusion 116 of the tray main body 110 is disposed at the opposite side of the tray main body 120 with respect to the connection protrusion 121 of the tray cover 120. Since the height of the separation protrusion 116 is greater than the height of the bio disc 10, although the tray cover 120 does not cover the entirety of the upper surface of the bio disc 10, damage to the exposed detection region 15 due to the inner surface of the pouch 20, as shown in FIG. 1, can be prevented.

The support protrusions 115 of the tray main body 110 and the support protrusion 123 of the tray cover 120 respectively support the lower and upper surfaces of the bio disc 10.

As is apparent from the above description, a detecting device packing tray in accordance with one exemplary embodiment allows a detecting device to be inserted into a pouch under the condition that the detecting device is fixed to a tray, thereby preventing random movement of the detecting device within the pouch and thus damage to the detecting device, i.e., scratches due to friction with the inner surface of the pouch. Further, although external impact is applied to the pouch in which the detecting device is packed, the tray serves to absorb the impact, thereby reducing damage to the detecting device.

Further, a detection region of the detecting device is protected by the tray and thus does not contact the pouch. In addition, the detection region does not contact the tray by a non-contact groove provided on the tray and thus is not damaged due to friction with the tray.

Moreover, since a dehumidifying agent is fixedly mounted on the tray, damage to the detecting device due to random movement of the dehumidifying agent is prevented.

Although a few exemplary embodiments have been shown and described, it would be appreciated by those skilled in the art that changes may be made in these embodiments without departing from the principles and spirit of the inventive concept, the scope of which is defined in the claims and their equivalents.

What is claimed is:

1. A detecting device packing tray comprising:
a tray main body configured to support a detecting device comprising a detection region to detect a reaction result, wherein the tray main body comprises:
a non-contact groove provided at a position corresponding to the detection region of the detecting device when the detecting device is supported by the tray main body so that the detection region does not contact the tray main body;
an inner support plane;
an outer support plane located radially outward from the inner support plane; and
a plurality of support protrusions each having a ring shape and provided between the inner support plane and the outer support plane; and
a tray cover that is connected to a first outer edge of the tray main body, and is configured to connect to a center region of the tray main body and to cover only a portion of the detecting device, wherein the tray cover does not extend to a second outer edge of the tray main body that is opposite to the first outer edge of the tray main body.

2. The detecting device packing tray according to claim 1, wherein the tray main body further comprises fixing protrusions configured to connect to a central hole of the detecting device so as to fix the detecting device.

3. The detecting device packing tray according to claim 1, wherein the non-contact groove has a ring shape.

4. The detecting device packing tray according to claim 1, further comprising a dehumidifying agent case which is configured to accommodate a dehumidifying agent.

5. The detecting device packing tray according to claim 4, wherein the dehumidifying agent case comprises a recess to accommodate the dehumidifying agent, and a cover configured to open and close an inlet of the recess.

6. The detecting device packing tray according to claim 5, wherein the cover is rotatably connected to the tray main body.

7. The detecting device packing tray according to claim 5, wherein the dehumidifying agent case further comprises a hole communicating an inner space of the recess with an outside of the dehumidifying agent accommodation recess.

8. The detecting device packing tray according to claim 2, wherein the tray cover is rotatably connected to the tray main body, and is configured to prevent separation of the detecting device from the tray main body.

9. The detecting device packing tray according to claim 8, wherein the tray cover comprises a connection protrusion configured to be connected to the fixing protrusions.

10. The detecting device packing tray according to claim 1, wherein:
the inner support plane is configured to support a central portion of the detecting device and the outer support plane is configured to support an edge portion of the detecting device; and
the non-contact groove is interposed between the inner support plane and the outer support plane in a radial direction of the detecting device.

11. The detecting device packing tray according to claim 10, wherein the tray main body further comprises:
- a separation protrusion disposed on the outer support plane; and
- a height of the separation protrusion is at least greater than a height of the detecting device.

12. A detecting device packing tray comprising:
a tray main body configured to support a lower surface of a detecting device, the tray main body comprising:
- an inner support plane configured to support the detecting device;
- an outer support plane configured to support the detecting device, wherein the outer support plane is provided a position radially outward from the inner support plane; and
- a plurality of support protrusions each having a ring shape and provided between the inner support plane and the outer support plane;
a non-contact groove interposed between the inner support plane and the outer support plane, wherein the non-contact groove does not contact the tray main body; and
a tray cover that is connected to a first outer edge of the tray main body, and is configured to connect to a center region of the tray main body and to cover only a portion of the detecting device, wherein the tray cover does not extend to a second outer edge of the tray main body that is opposite to the first outer edge of the tray main body.

13. The packing tray according to claim 12, wherein the non-contact groove has a ring shape.

14. A detecting device packing tray comprising:
a tray main body configured to support a lower surface of a detecting device, the tray main body comprising:
- a plurality of fixing protrusions configured to connect to a central hole of the detecting device to fix the detecting device to the tray main body;
- a non-contact groove configured so that at least a part of the lower surface of the detecting device does not contact the tray main body;
- an inner support plane;
- an outer support plane located radially outward from the inner support plane; and
- a plurality of support protrusions each having a ring shape and provided between the inner support plane and the outer support plane;
a tray cover rotatably connected to the tray main body so as to cover at least a part of an upper surface of the detecting device when the detecting device is supported by the tray main body, wherein the tray cover is connected to a first outer edge of the tray main body, and is configured to connect to a center region of the tray main body and to cover only a portion of the detecting device, wherein the tray cover does not extend to a second outer edge of the tray main body that is opposite to the first outer edge of the tray main body.

15. A packing tray comprising:
a tray main body configured to support a lower surface of a detecting device, the tray main body comprising:
- an inner support plane;
- an outer support plane located radially outward from the inner support plane;
- a plurality of support protrusions each having a ring shape and provided between the inner support plane and the outer support plane;
- at least one fixing protrusion which extends from the inner support plane; and
- a groove which has a ring shape and is provided between the outer support plane and an outermost support protrusion from among the plurality of support protrusions;
a tray cover which is connected to the tray main body and is configured to fold over the train main body to cover a portion of the tray main body, wherein the tray cover is connected to a first outer edge of the tray main body, and is configured to connect to a center region of the tray main body and to cover only a portion of the detecting device, wherein the tray cover does not extend to a second outer edge of the tray main body that is opposite to the first outer edge of the tray main body.

16. The packing tray according to claim 15, further comprising a dehumidifying agent case which is disposed on the tray main body and configured to accommodate a dehumidifying agent.

* * * * *